United States Patent [19]

Shroot et al.

[11] Patent Number: 4,581,380

[45] Date of Patent: Apr. 8, 1986

[54] 2,6-DISUBSTITUTED NAPHTHALENE DERIVATIVES, A PROCESS FOR PREPARING THE SAME AND PHARMACEUTICAL AND COSMETIC COMPOSITIONS CONTAINING THE SAME

[75] Inventors: Braham Shroot, Antibes; Jacques Eustache, Grasse; Martine Bouclier, Antibes, all of France

[73] Assignee: Groupement Economique dite: Centre National de Recherches Dermatologiques C.I.R.D., Valbonne, France

[21] Appl. No.: 675,701

[22] Filed: Nov. 28, 1984

[30] Foreign Application Priority Data

Nov. 28, 1983 [FR] France .................. 83 18917

[51] Int. Cl.[4] ............. A01N 35/04; A01N 31/08; C07C 39/17; C07C 47/546
[52] U.S. Cl. .................................. 514/700; 568/328; 568/440; 568/735; 568/808; 585/425; 585/427; 514/729; 514/765; 514/846; 558/411
[58] Field of Search ........ 585/425, 427; 568/328, 260/465 R; 515/700, 729, 765, 846

[56] References Cited

U.S. PATENT DOCUMENTS 4,454,341  6/1984  Dawson et al. ............... 560/100

*Primary Examiner*—Dolph H. Torrence
*Attorney, Agent, or Firm*—Cushman, Darby & Cushman

[57] ABSTRACT

New 2,6-disubstituted derivatives of naphthalene have the formula

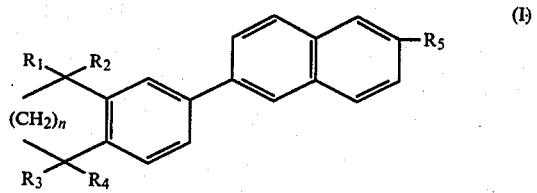

wherein
n is 1 or 2,
$R_1$ to $R_4$ are hydrogen or $CH_3$,
$R_5$ is (i)

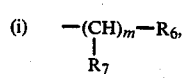

(ii)

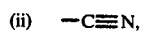

(iii)

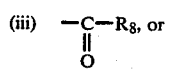

(iv) 2-oxazolinyl, wherein m is 0 or 1, $R_6$ is hydrogen, alkyl, $OR_9$ wherein $R_9$ is H, alkyl or

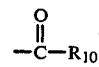

wherein $R_{10}$ is alkyl or aryl, or $R_6$ is

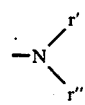

when m=1, r' and r" representing H, alkyl, mono- or poly-hydroxyalkyl, aryl or a heterocycle when taken together, $R_7$ is H or alkyl, $R_8$ is H, alkyl and the acetal of said compounds, and the salts of the compounds of formula I. These compounds are usefully employed in the pharmaceutical and cosmetic fields.

11 Claims, No Drawings

2,6-DISUBSTITUTED NAPHTHALENE DERIVATIVES, A PROCESS FOR PREPARING THE SAME AND PHARMACEUTICAL AND COSMETIC COMPOSITIONS CONTAINING THE SAME

The present invention relates to naphthalene derivatives, their process of preparation and their use in pharmaceutical and cosmetic formulations.

These new naphthalene derivatives can be classified with compounds known as "retinoids" of which the most well known are trans and cis retinoic acids (tretinoin and isotretinoin) and etretinate.

Relative to the retinoids the 2,6 disubstituted naphthalene derivatives according to the present invention, due to their structure, exhibit better stability to light and to oxygen. Moreover, they exhibit an increased activity in topical and systemic treatments of dermatological diseases which are associated with keratinization disorders (differentiation-poliferation) and dermatological diseases or others with anti-inflammatory component as well as an anti-inflammatory activity.

These novel 2,6-disubstituted naphthalene derivatives can be represented by the following general formula

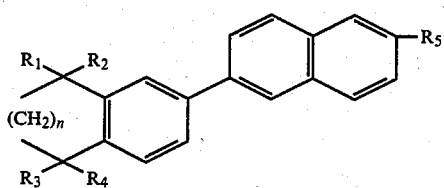

wherein
n is 1 or 2,
$R_1$, $R_2$, $R_3$ and $R_4$ each independently represent hydrogen or methyl,
$R_5$ represents (i) 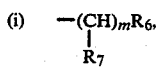

(ii) $-C \equiv N$, (iii) 

(iv) 2-oxazolinyl,
wherein
m is 0 or 1, $R_6$ represents (a) hydrogen, (b) lower alkyl, (c) $-OR_9$ wherein $R_9$ represents hydrogen, lower alkyl,

wherein $R_{10}$ represents alkyl having 1–10 carbon atoms or aryl, or (d)

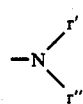

when m=1, r' and r" representing hydrogen, lower alkyl, mono- or poly-hydroxy alkyl, aryl optionally substituted or taken together forming a heterocycle, $R_7$ represents hydrogen or lower alkyl, $R_8$ represents hydrogen, lower alkyl and the corresponding acetals of said carbonyl containing compounds and the salts of said compounds of formula I.

By lower alkyl is meant radicals having 1–6 carbon atoms, principally, methyl, ethyl, isopropyl, butyl and tert. butyl.

By monohydroxy alkyl is meant radicals having 2 or 3 carbon atoms, principally 2-hydroxyethyl and 2-hydroxypropyl.

By polyhydroxy alkyl is meant a radical having from 3 to 6 carbon atoms and 2 to 5 hydroxy groups such as 2,3-dihydroxy propyl, 2,3,4-trihydroxybutyl or 2,3,4,5-tetrahydroxy pentyl.

By aryl is meant a phenyl radical optionally substituted by halogen, hydroxy or a nitro function.

By aralkyl is meant a benzyl radical or a phenethyl radical.

When the radicals r' and r" taken together with the nitrogen atom to which they are attached form a heterocycle, the heterocycle can be piperidino, piperazino, morpholino or pyrolidino.

When the radical $R_8$ represents hydrogen or lower alkyl, the acetals are lower dialkyl acetals such as dimethyl- or diethyl-acetals.

Representative compounds of formula I include the following:

6-(5,6,7,8-tetrahydro-5,5,8,8-tetramethyl-2-naphthyl)-2-naphthalene methanol;

1'α-methyl-6-(5,6,7,8-tetrahydro-5,5,-8,8-tetramethyl-2-naphthyl)-2-naphthalene methanol;

1'α-ethyl-6-(5,6,7,8-tetrahydro-5,5,8,8-tetramethyl-2-naphthyl)-2-naphthalene methanol;

1'α-n-propyl-6-(5,6,7,8-tetrahydro-5,5,8,8-tetramethyl-2-naphthyl)-2-naphthalene methanol;

methyl 6-(5,6,7,8-tetrahydro-5,5,8,8-tetramethyl-2-naphthyl)-2-naphthyl methylether;

ethyl 6-(5,6,7,8-tetrahydro-5,5,8,8-tetramethyl-2-naphthyl)-2-naphthyl methylether;

6-(5,6,7,8-tetrahydro-5,5,8,8-tetramethyl-2-naphthyl)-2-naphthol;

methyl 6-(5,6,7,8-tetrahydro-5,5,8,8-tetramethyl-2-naphthyl)-2 naphthyl ketone;

ethyl 6-(5,6,7,8-tetrahydro-5,5,8,8-tetramethyl-2-naphthyl)-2-naphthyl ketone;

6-(5,6,7,8-tetrahydro-5,5,8,8-tetramethyl-2-naphthyl)-2-naphthaldehyde;

6-(5,6,7,8-tetrahydro-5,5,8,8-tetramethyl-2-naphthyl)-2-naphthyl methyl acetate;

6-(5,6,7,8-tetrahydro-5,5,8,8-tetramethyl-2-naphthyl)-2-naphthyl methyl propionate;

1'α-methyl-6-(5,6,7,8-tetrahydro-5,5,8,8-tetramethyl-2-naphthyl)-2-naphthyl methyl acetate;

1'α-methyl-6-(5,6,7,8-tetrahydro-5,5,8,8-tetramethyl-2-naphthyl)-2-naphthyl methyl propionate and 2-methyl-6-(5,6,7,8-tetrahydro-5,5,8,8-tetramethyl-2-naphthyl)-2-naphthalene.

Particularly preferred compounds of formula I according to the present invention are those wherein the $R_1$, $R_2$, $R_3$ and $R_4$ radicals represent methyl, n is 2 and $R_5$ represents either (i)

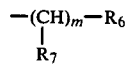

wherein m is 0 or 1, $R_7$ represents hydrogen, and $R_6$ represents hydrogen or $-OR_9$ wherein $R_9$ is hydrogen, or (ii) the radical,

wherein $R_8$ is hydrogen.

Representative ones of these preferred compounds include principally:

6-(5,6,7,8-tetrahydro-5,5,8,8-tetramethyl-2-naphthyl)-2-naphthalene methanol;

6-(5,6,7,8-tetrahydro-5,5,8,8-tetramethyl-2-naphthyl)-2-naphthol;

6-(5,6,7,8-tetrahydro-5,5,8,8-tetramethyl-2-naphthyl)-naphthaldehyde and 2-methyl-6-(5,6,7,8-tetrahydro-5,5,8,8-tetramethyl-2-naphthyl)-2-naphthalene.

The compounds according to the present invention are obtained by a coupling reaction between a halogenated compound corresponding to formula II and a halogenated derivative of naphthalene corresponding to formula III:

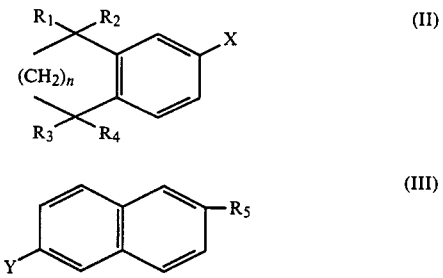

wherein $R_1$ to $R_5$ and n have the same meanings as those given above for formula I and X and Y represent Cl, Br, F and I.

According to this coupling reaction, the halogenated compound of formula II is transformed into its magnesium, lithium or zinc form in accordance with methods known in the literature and is coupled with the halogenated naphthalene derivative of formula III by employing, as a reaction catalyst, a transition metal or one of its complexes.

Representative reaction catalysts include, in particular, derivatives of nickel or palladium and in particular the complexes of $Ni^{II}$ ($NiCl_2$) with various phosphines.

The coupling reaction is generally carried out at a temperature between $-20°$ and $+30°$ C. in an anhydrous solvent such as, for example, dimethyl formamide or tetrahydrofuran.

The resulting product can be purified by recrystallization or by silica column chromatography.

It goes without saying that the selection of the halogenated naphthalene derivative of formula III for the coupling reaction with the halogenated compound of formula II must be such that it leads, by subsequent reaction, to the various meanings of the $R_5$ radical given above.

To this end particularly appropriate halogenated naphthalene derivatives are the t-butyl dimethyl silic ether of 6-bromo-2-naphthalene methanol or the t-butyl dimethyl silic ether of 6-bromo-2-naphthol.

The halogenated compounds of formula II are for the most part known and have been described in U.S. Pat. No. 3,499,751, principally those in which n=2, i.e. the 2-chloro- or 2-bromo-5,6,7,8-tetramethyl-5,5,8,8-tetrahydronaphthalene.

When the compounds according to the invention are provided in the salt form, it is a question of salts of mineral or organic acids, principally the hydrochlorides, hydrobromides or citrates.

The present invention also relates to, as medicines, the compounds of formula I and/or their salts as defined above.

These compounds exhibit good activity in the test for inhibiting ornithine decarboxylase after induction, by "tape stripping" the body of a nude rat. This test is considered a measure of the action of retinoids with regard to cellular proliferation phenomenon.

These compounds are particularly suitable indeed for treating dermatological diseases linked to a keratinization disorder (differentiation, proliferation) as well as dermatological diseases or others with inflammatory components such as principally:

acne vulgaris, black heads or polymorphous, solar acne seniles, and medicamental or professional acne;

extensive and/or severe forms of psoriasis, and other keratinization disorders, and principally ichtyosis and ichtyosiform states, Darier disease, palmo-planatary keratodermy, leucoplasies and leucoplasiform states, lichen plane, all benign or malignant dermatologic proliferations, severe or extended.

They are also active for certain rheumatic diseases principally psoriasic rheumatism. The present invention has then also for an object medicinal compositions containing at least one compound of formula I and/or one of its salts such as defined above.

The present invention also relates to new medicinal compositions which are intended principally for the above mentioned diseases characterized by the fact that they include, in a pharmaceutically acceptable support, at least one compound of formula I.

As has been indicated previously, the heterocyclic derivatives according to the present invention exhibit, relative to known retinoids, better stability against light and oxygen, this being essentially due to the fact that they do not possess an easily isomerized double bond.

Besides the irritation test on a rabbit has shown that the compounds of formula I are less irritating than retinoic acid.

The compounds according to the present invention are generally administered at a daily dosage of about 2 μg/kg to 2 mg/kg and preferably from 10 to 100 μg/kg.

As vehicles or supports for the compositions there can be employed any conventional support, the active compound being found either in the dissolved state or in the dispersed state in the support.

The compositions can be administered enterally, parenterally or topically. When administered enterally, the medicines can be provided in the form of tablets, gels, pills, syrups, suspensions, solutions, powders, granules or emulsions. When administered parenterally, the compositions can be provided in the form of solutions for perfusion or injection.

When administered topically, the pharmaceutical compositions based on the compounds according to the present invention can be provided in the form of ointments, tinctures, creams, solutions, lotions, gels, pommades, powders, impregnated pads or buffers, sprays or even suspensions.

The compositions for topical application contain preferably from 0.0005 to about 5 weight percent of the compound of formula I.

These compositions for topical application can be provided either in anhydrous form or in aqueous form according to clinical indication and can contain other components.

The compounds of formula I and/or their salts according to the present invention also find use in the field of cosmetics, in particular in body and hair hygiene and principally for acne, for regrowth of hair and preventing its falling, to combat against the oily appearance of the skin or hair or in the protection against the adverse effects of the sun, or again to combat against physiologically dry skin.

The present invention envisages then a cosmetic composition containing, in a cosmetically acceptable vehicle, at least one compound of formula I, this composition being provided principally in the form of a lotion, gel, soap or shampoo.

The concentration of the compound(s) of formula I in cosmetic compositions is between 0.0005 and 2 weight percent and preferably between 0.01 and 1 weight percent.

The medicinal and cosmetic compositions according to the present invention can contain inert or even pharmacodynamic or cosmetically active additives and principally: hydrating agents such as thiamorpholinone and its derivatives, or urea, anti-seborrheic agents such as S-carboxymethyl cysteine, S-benzyl cysteamine and their derivatives, thioxolone, antibiotics as erythromycin, neomycin and tetracyclines, agents favoring the regrowth of hair, as "Minoxidil" (2,4-diamino-6-piperidino-3-pyrimidine oxide) and its derivatives; anthralin and its derivatives; Diazoxide; Phenytoin and oxapropanium iodide; steroidic and non-steroidic anti-inflammatory agents; carotenoids and principally, $\beta$-carotene; anti-psoriasic agents such as authralin and its derivatives, 5,8,11,14 eicosatetraynoic acid and 5,8,11 trinoic acid.

The compositions according to the invention can also contain flavor improving agents, preservatives, stabilizers, humidity regulating agents, pH regulating agents, osmotic pressure modifying agents, emulsifiers, UV-A and UV-B filters, antioxidants such as $\alpha$-tocopherol, butylhydroxyanisol or butylhydroxy toluene.

The following non-limiting examples are given to illustrate the preparation of the active compounds of formula I according to the present invention.

EXAMPLE 1

6-(5,6,7,8-tetrahydro-5,5,8,8-tetramethyl-2-naphthyl)-2-naphthalene methanol (a) Preparation of t-butyl dimethylsilic ether of 6-bromo-2-naphthalene methanol A solution of 6-bromo-2-naphthalene methanol (1.721 g; 7.26 moles), pyridine (0.760 ml), 4-dimethylaminopyridine (150 mg) and t-butyl dimethyl silyl chloride (1.42 g; 1.1 equivalent) in a mixture of dichloromethane (15 ml) and tetrahydrofuran (15 ml) is stirred for 16 hours at 20° C. under nitrogen and then for 2 hours at reflux. The solvents are evaporated under reduced pressure, the residue being taken up three times with 15 ml of a heptane (2/3 v/v) ether (1/3 v/v) mixture. The resulting solution is filtered under reduced pressure through a silica column (3×10 cm); one uses for elution 150 ml of the same heptane-ether mixture. The solvents are evaporated under reduced pressure at 30° C., then the residue is dried under vacuum at 90° C. for ½ hour. There is thus obtained an oil which crystallizes on cooling. The t-butyl dimethyl silic ether of 6-bromo-2-naphthalene methanol is pure and has a melting point of 74°–75° C. yield: 2.42 g (95%) RF: 0.85 (Merck silica plates) the eluant being a mixture of diethyl ether (50%) and hexane (50%).

(b) Preparation of t-butyl-dimethyl silic ether of 6-(5,6,7,8-tetrahydro-5,5,8,8-tetramethyl-2-naphthyl)-2-naphthalene methanol.

1.556 g (5.83 mmoles) of 5,6,7,8-tetrahydro-5,5,8,8-tetramethyl-2-bromo naphthalene are dissolved in tetrahydrofuran, THF, (10 ml) to which is then added 0.147 g (1.1 equivalents) of powdered magnesium. The reaction mixture is then heated under nitrogen at 60° C. for 2 hours, at which point the resulting solution is cooled to 20° C. and to which is then added the compound obtained in part (a) above (1.760 g, 5 mmoles) and the

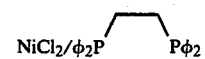

complex (40 mg, 0.075 mmole). The reaction mixture is then stirred for one hour at ambient temperature. The mineral residues are removed by filtration under reduced pressure through a silica column (3×10 cm) using a mixture of 88% heptane, 10% dichloromethane and 2% ether as eluant. The solvents are evaporated, and the residue chromatographed on silica (Waters "Prep 500", 1 column) by using as eluant a mixture of 90% isooctane and 10% dichloromethane. After evaporation of the solvents and drying under a vacuum at 90° C., for 1 hour, there is obtained the pure expected product which crystallizes on cooling. Yield: 1.541 g (67%) RF: 0.90 (Merck silica plates), the eluant being a mixture of 50% diethyl ether and 50% hexane.

(c) 1.429 g (3.11 mmoles) of the product obtained above in part (b) are dissolved in THF (6 ml), to which are added 20 ml of methanol and 700 mg (4.66 mmoles) of cesium fluoride. The resulting reaction mixture is heated at reflux for 24 hours at which point it is poured into a mixture of 100 ml of ether and 100 ml of water. The ether phase is recovered and washed with water (2×100 ml). After drying and evaporation of the solvents the residue is dissolved in 10 ml of dichloromethane and thereafter filtered under reduced pressure through a silica column (3×10 cm), and washed initially with hexane (200 ml), the hexane phase being removed, then with a mixture of 90% dichloromethane and 10% ether (100 ml) that is then dried. After evaporation of the solvents, there is obtained a crystalline product which is dried under a vacuum at 80° C. for 11 hours, yielding 1.032 g of pure product (96%). Melting point 175° C. RF: 0.35 (Merck silica plates), the eluant being a mixture of diethyl ether (50%) and hexane (50%).

EXAMPLE 2

6-(5,6,7,8-tetrahydro-5,5,8,8-tetramethyl-2-naphthyl)-2-naphthaldehyde 256 mg (0.74 mmole) of the compound obtained in Example 1, part (c), are dissolved in 10 ml of dichloromethane, to which is added 382 mg (2.4 equivalents) of pyridinium chlorochromate. The resulting reaction mixture is stirred for 1 hour at 20° C. and then filtered under reduced pressure through a silica column (3×10 cm) by using a mixture of 90% dichloromethane and 10% ether as eluant. The product is purified by preparative HPLC (silica column) and there are obtained 191 mg (75%) of product having a melting point 192° C. RF: 0.7 (Merck silica plates), the eluant being a mixture of diethyl ether (50%) and hexane (50%).

EXAMPLE 3

2 methyl-6-(5,6,7,8-tetrahydro-5,5,8,8-tetramethyl-2-naphthyl)-2-naphthalene In accordance with the same procedures as in Example 1, part (b), starting with 2-methyl-6-bromonaphthalene (2.21 g, 10 mmoles) and 5,6,7,8-tetrahydro-5,5,8,8-tetramethyl-2-bromonaphthalene (3.20 g, 12 mmoles), there is obtained after column chromatography (9 hexane, 1 dichloromethane) 2-methyl-6-(5,6,7,8-tetrahydro-5,5,8,8-tetramethyl-2-naphthyl)naphthalene (2.38 g, 72%) having a melting point of 173°–175° C.

EXAMPLE 4

6-(5,6,7,8-tetrahydro-5,5,8,8-tetramethyl-2-naphthyl)-2-naphthol (a) Preparation of t-butyl dimethyl silic ether of 6-bromo-2-naphthol.

To a solution of 6-bromo-2-naphthol (3 g, 13.5 mmoles) in 25 ml of dimethyl formamide containing 60 mg (0.5 mmole) of 4-dimethylamino-pyridine, there are added 2.11 g (14 mmoles) of t-butyl-dimethylsilyl chloride, and the resulting mixture is stirred for 48 hours at ambient temperature and then poured into water acidified with molar sulfuric acid up to pH 2 and finally extracted with diethyl ether. The organic phase is washed with water, dried and concentrated under a vacuum. The orange oil thus obtained is filtered under reduced pressure through a short silica column (3×10 cm), using hexane as the eluant. The pale yellow oil thus obtained crystallizes and is dried under a vacuum, thus providing t-butyl dimethylsilic ether of 6-bromo-2-naphthol having a melting point of 62° C. (3.4 g, 75%).

(b) Preparation of t-butyl dimethylsilic ether of 6-(5,6,7,8-tetrahydro-5,5,8,8-tetramethyl-2-naphthyl)-2-naphthol.

In accordance with the same procedures as in Example 1, part (b), by starting with 5,6,7,8-tetrahydro-5,5,8,8-tetramethyl-2-bromonaphthalene (1 g, 3.75 mmoles) and t-butyl dimethylsilic ether of 6-bromo-2-naphthol (1.00 g, 3 mmoles) there are obtained 1.100 g (yield: 82%) of t-butyl-dimethylsilic ether of 6-(5,6,7,8-tetrahydro-5,5,8,8-tetramethyl-2-naphthyl)-2-naphthol having a melting point of 115°–118° C. Rf: 0.35 (Merck silica plates, the eluant being a 9:1 mixture of hexane:dichloromethane).

(c) In accordance with the same procedures as in Example 1, part (c), by starting with 0.49 g (1.1 mmoles) of t-butyl-dimethylsilic ether of 6-(5,6,7,8-tetrahydro-5,5,8,8-tetramethyl-2-naphthyl)-2-naphthol, there is obtained 0.365 g (100 %) of 6-(5,6,7,8-tetrahydro-5,5,8,8-tetramethyl-2-naphthyl)-2-naphthol having a melting point of 104° C.

The following non-limiting examples illustrate compositions prepared in accordance with the present invention.

Composition Examples

A—For oral administration

| Example (a) - a 0.2 g tablet | |
|---|---|
| Compound of Example 2 | 0.001 g |
| Starch | 0.114 g |
| Bicalcium phosphate | 0.020 g |
| Silica | 0.020 g |
| Lactose | 0.030 g |
| Talc | 0.010 g |
| Magnesium stearate | 0.005 g |
| Example (b) - a 0.5 g gel - Formula of the powder | |
| Compound of Example 2 | 0.001 g |
| Cornstarch | 0.150 g |
| Magnesium stearate | 0.250 g |
| Sucrose, sufficient amount for | 0.500 g |

The powder is packaged in a gel composed of gelatin and titanium dioxide.

| Example (c) - a 0.4 g capsule containing a suspension | |
|---|---|
| Compound of Example 3 | 0.005 g |
| Glycerine | 0.200 g |
| Sucrose | 0.050 g |
| Polyethylene glycol 400 | 0.050 g |
| Purified water, sufficient amount for | 0.400 g |

This suspension is packaged in a capsule composed of gelatin, glucerine, titanium dioxide and water.

| Example (d) - Drinkable suspension in 5 ml ampoules | |
|---|---|
| Compound of Example 2 | 0.001 g |
| Glycerine | 0.500 g |
| Sorbitol (70%) | 0.500 g |
| Sodium saccharinate | 0.010 g |
| Methyl para-hydroxybenzoate | 0.040 g |
| Aroma agent, sufficient amount | |
| Purified water, sufficient amount for | 5.000 ml |

B—For topical application

| Example (e) - Ointment | |
|---|---|
| Compound of Example 2 | 0.001 g |
| Stearyl alcohol | 3.000 g |
| Lanolin | 5.000 g |
| Petrolatum | 15.000 g |
| Distilled water, sufficient amount for | 100.000 g |
| Example (f) - non-ionic oil-in-water cream | |
| Compound of Example 1 | 0.050 g |
| Cetylalcohol | 3.000 g |
| Stearyl alcohol | 3.400 g |
| Cetyl alcohol oxyethylenated with 20 moles of ethylene oxide | 0.630 g |
| Stearyl alcohol oxyethylenated with 20 moles of ethylene oxide | 1.470 g |
| Glycerol monostearate | 2.000 g |
| Petrolatum oil | 15.000 g |
| Glycerine | 10.000 g |
| Preservative, sufficient | |

| -continued | |
|---|---|
| amount | |
| Distilled water, sufficient amount for | 100.000 g |
| Example (g) - Ointment | |
| Compound of Example 4 | 0.020 g |
| Isopropyl myristate | 81.700 g |
| Liquid petrolatum oil | 9.100 g |
| Silica, sold under the name "Aerosil 200" by Degussa | 9.180 g |
| Example (h) - Anionic oil-in-water cream | |
| Compound of Example 2 | 0.010 g |
| Sodium dodecyl sulfate | 0.800 g |
| Glycerol | 2.000 g |
| Stearyl alcohol | 20.000 g |
| Triglycerides of capric/ caprylic acids sold under the name "Miglyol 812" by Dynamit Nobel | 20.000 g |
| Preservative, sufficient amount | |
| Demineralized water, sufficient amount for | 100.000 g |
| Example (i) - Gel | |
| Compound of Example 4 | 0.005 g |
| Hydroxypropyl cellulose, sold under the name of "Klucel HF" by Hercules | 2.000 g |
| Water/ethanol, 50:50, sufficient amount for | 100.000 g |

What is claimed is:

1. A naphthalene derivative having the formula:

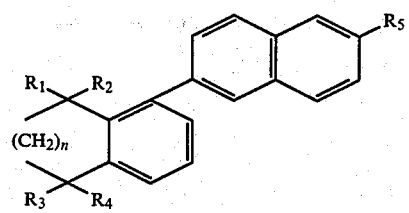

wherein
$R_1$, $R_2$, $R_3$ and $R_4$ represent methyl,
n is 2, and
$R_5$ is selected from the group consisting of (i)

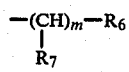

wherein m is 0 or 1,
$R_6$ is selected from the group consisting of hydrogen and $-OR_9$ wherein $R_9$ is hydrogen, and $R_7$ is hydrogen, and (ii)

wherein $R_8$ is hydrogen.

2. The naphthalene derivative of claim 1 selected from the group consisting of:

6-(5,6,7,8-tetrahydro-5,5,8,8-tetramethyl-2-naphthyl)-2-naphthalene methanol,
6-(5,6,7,8-tetrahydro-5,5,8,8-tetramethyl-2-naphthyl)-2-naphthol,
6-(5,6,7,8-tetrahydro-5,5,8,8-tetramethyl-2-naphthyl)-2-naphthaldehyde, and
2-methyl-6-(5,6,7,8-tetrahydro-5,5,8,8-tetramethyl-2-naphthyl)-2-naphthalene.

3. A process for preparing the naphthalene derivative of claim 1 comprising coupling in an anhydrous solvent medium and in the presence of, as a reaction catalyst, a transition metal or a complex thereof, the magnesium, lithium or zinc form of a compound having the formula

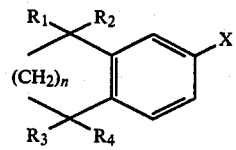

with a halogenated compound having the formula

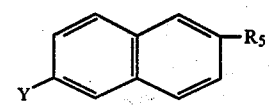

wherein
n, $R_1$, $R_2$, $R_3$, $R_4$ and $R_5$ have the meanings given in claim 1 and
X and Y represent Cl, Br, F or I.

4. The process of claim 3 wherein the coupling reaction is carried out at a temperature ranging from $-20°$ to $+30°$ C.

5. A medicine comprising the naphthalene derivitive of claim 1.

6. A pharmaceutical composition comprising in a pharmaceutically acceptable carrier capable of being administered enterally, parenterally or topically, at least one naphthalene derivative of claim 1.

7. The composition of claim 6 characterized by the fact that it is administered at a rate of a daily dosage of about 2 µg/kg of the said naphthalene derivative or a salt thereof.

8. The composition of claim 6 in a topically applicable form containing from 0.0005 to 5 weight percent of said naphthalene derivative.

9. A cosmetic composition comprising in a cosmetically acceptable carrier at least one naphthalene derivative of claim 1 or a salt thereof.

10. The composition of claim 9 wherein said naphthalene derivative is present in an amount ranging from 0.0005 to 2 weight percent based on the total weight of said composition.

11. The composition of claim 9 wherein said naphthalene derivative is present in an amount ranging from 0.01 to 1 weight percent based on the total weight of said composition.

* * * * *

UNITED STATES PATENT AND TRADEMARK OFFICE
CERTIFICATE OF CORRECTION

PATENT NO. : 4,581,380    Page 1 of 2

DATED : April 8, 1986

INVENTOR(S) : Braham Shroot et al.

It is certified that error appears in the above-identified patent and that said Letters Patent is hereby corrected as shown below:

IN THE HEADING:

Correct the assignee's name to read --

Groupement Economique dite: Centre International
De Recherches Dermatologiques C.I.R.D. --

IN THE CLAIMS:

Claim 1, line 2 (Col. 9, between lines 31 and 40) the structural formula should read

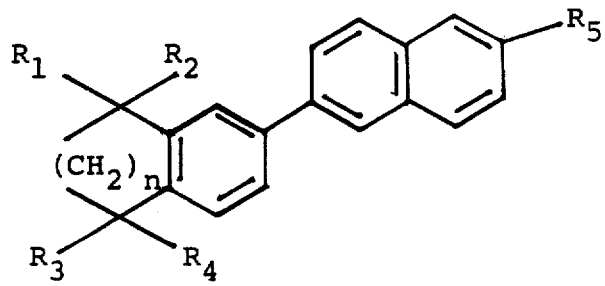

UNITED STATES PATENT AND TRADEMARK OFFICE
CERTIFICATE OF CORRECTION

PATENT NO. : 4,581,380  Page 2 of 2

DATED : April 8, 1986

INVENTOR(S) : Braham Shroot et al.

It is certified that error appears in the above-identified patent and that said Letters Patent is hereby corrected as shown below:

Claim 5, line 2 (Col. 10, line 37) change "derivitive" to read

-- derivative --.

Signed and Sealed this

Thirteenth Day of October, 1987

Attest:

DONALD J. QUIGG

Attesting Officer

Commissioner of Patents and Trademarks